United States Patent [19]

Grund et al.

[11] Patent Number: 5,093,514

[45] Date of Patent: Mar. 3, 1992

[54] BASE-CATALYZED DEHYDRATION OF SUBSTITUTED CIS-1,2-DIHYDROXYCYCLOHEXA-3,5-DIENES

[75] Inventors: Alan D. Grund; Ronald J. Huss, both of Manitowoc; Michael H. Reimer, Sheboygan, all of Wis.

[73] Assignee: E. I. Du Pont de Nemours and Company, Wilmington, Del.

[21] Appl. No.: 623,584

[22] Filed: Dec. 7, 1990

[51] Int. Cl.[5] ............................................. C07C 255/00
[52] U.S. Cl. ................................. 558/423; 568/747; 568/780
[58] Field of Search ................... 568/747, 780; 558/423

[56] References Cited

U.S. PATENT DOCUMENTS 4,590,304  5/1986  Wallace et al. ................. 568/780

FOREIGN PATENT DOCUMENTS 2203150  5/1991  United Kingdom .

OTHER PUBLICATIONS

Wessely et al., Chemical Abstracts, vol. 54, No. 2229b (1960).

*Primary Examiner*—Bruce Gray

*Attorney, Agent, or Firm*—Charles E. Krukiel

[57] ABSTRACT

A process for dehydrating compounds of the formula

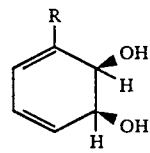

where —R is —CH=CH$_2$, —C≡CH —C≡N or

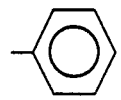

in an aqueous solution thereof is disclosed. In the case where R is —CH=CH$_2$ or —C≡CH, the temperature is preferably at least 50° C. and preferably 75° to 100° C. The base is at least 0.1N and preferably 1.0 to 8N. Preferred bases are NaOH, KOH and C$_5$OH. In the case where —R is C≡N, the temperature preferably is 20° to 50° C.

10 Claims, No Drawings

BASE-CATALYZED DEHYDRATION OF SUBSTITUTED CIS-1,2-DIHYDROXYCYCLOHEXA-3,5-DIENES

This invention was made with Government support under contract number F33615-89-C-5601 awarded by the U.S. Air Force. The Government has certain rights in the invention.

FIELD OF THE INVENTION

The present invention relates to the dehydration of various substituted cis-1,2-dihydroxycyclohexa-3,5-dienes to form the corresponding m-substituted phenols. The use of a base, optionally at elevated temperature optimizes production of the m-substituted phenols over the o-substituted phenols.

BACKGROUND OF THE INVENTION

Compounds of the general formula

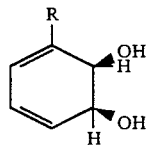

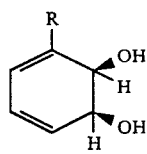

have been chemically dehydrated to phenols by acidification. In general, the 2-hydroxy isomer predominates, or is the exclusive product of the reaction. The present invention relates to the use of a base to optimize production of the 3-hydroxy isomer of certain such compounds.

U.S. Pat. No. 4,508,822 discloses the preparation of compounds of the general formula

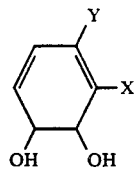

wherein X and Y may be the same or different, and represent hydrogen, halogen, ceryl, or cyano groups except that X and Y cannot both be hydrogen, using strains of Pseudomonas putida.

U.S. Pat. No. 4,532,209 discloses the production of p-cresol by the acidification of an aqueous solution of 4-methylcyclohexa-3,5-diene-1,2-diol-1-carboxylic acid.

Formation of (+)-cis-2,3-dihydroxy-1-methylcyclohexa-4,6-diene from Toluene by Pseudomonas putia, by D. T. Gibson et al., Biochemistry, pp. 1626–1630, Vol. 9, (1970) discloses the acid catalyzed dehydration of (+)-cis-2,3-dihydroxy-1-methylcyclohexa -4,6-diene.

U.K. Patent No. 2,203,150 B discloses preparing fluorophenols by dehydrating 1,2-dihydroxy-3-fluorocyclohexa-3,5-diene in the presence of base and subsequently recovering 2 and/or 3-fluorophenol. The use of base does not make the reaction overly selective for 3-fluorophenol.

Initial Reactions in the Oxidation of Ethylbenzene by Pseudomonas putida, by D. T. Gibson et al., Biochemistry, pp. 1520–1527, Vol. 12, No. 8, (1973) discloses the oxidation of ethyl benzene to (+)-cis-3-ethyl-3,5-cyclohexadiene-1,2-diol and (+)-cis-3-(1'-hydroxyethyl)-3,5-cyclohexadiene-1,2-diol by Pseudomonas putida as well as the oxidation of acetophenone to cis-3 (1'-oxoethyl)-3,5-cyclohexadiene -1,2-diol. The reference also discloses the acid catalyzed dehydration of (+)-cis-3-ethyl-3,5-cyclohexa-diene-1,2-diol.

Biodegradations Yield Novel Intermediates For Chemical Synthesis, D. W. Ribbons et al., Biotechnology and Biodegradations, pp. 213–245, London discloses the use of mutants of P. putida to form compounds of the formula

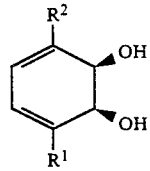

where $R^1=R^2=H$; $R^1=Cl$, $R^2=H$; $R^1=F$, $R^2=H$; $R^1=CH_3$, $R^2$-H; $R^1=Ph$, $R^2=H$; $R^1=CF_3$, $R^2=H$; $R1=C2H5$, $R^2=H$; $R^1=HC=CH_2$, $R^2=H$; $R^1=C\equiv CH$, $R^2=H$; $R^1=CH_3$, $R^2=F$; $R^1=CH_3$, $R^2=Cl$; $R^1=CH_3$, $R^2=Br$.

SUMMARY OF THE INVENTION

The present invention relates to the base catalyzed dehydration of compounds of the formula

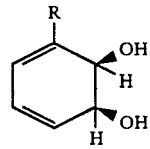

here —R is —CH=CH$_2$, —CH≡CH, or —C≡N, to form a compound of the formula

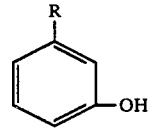

DETAILED DESCRIPTION

Generally a cell-free aqueous broth containing a cis-dihydrodiol at a concentration in the range of 200–5,000 parts per million (ppm) is used. To optimize dehydration to the meta isomer when —R is —CH=CH$_2$, or —C≡CH, the broth is quickly heated to at least 50° C. and preferably to from 75° to 100° C. In the case where —R is —C≡N the reaction is preferably performed at 20° to 50° C. Then a solution of alkali at the elevated temperature is quickly added and mixed. The final concentration of alkali is at least 0.1N, preferably 1.0N or higher such as up to 8N. The solution is held at the elevated temperature at least 15 minutes and preferably one hour or even longer such as up to 10 hours. The mixture is then cooled to 20 to 30° C. and the phenols recovered such as by extraction. The preferred bases are sodium hydroxide, potassium hydroxide and cesium hydroxide with sodium hydroxide being preferred because of cost.

The compounds produced by the process are useful as intermediates for producing polymeric materials.

EXAMPLES

In the Examples an aqueous solution of 500 ppm of the starting material was treated with reagents reported in the Tables to bring the normality of the overall solution to the value reported. In the Tables RT stands for room temperature.

EXAMPLE 1

Treatment of 2,3-dihydroxy-1-ethynylcyclohexa-4,6-diene.

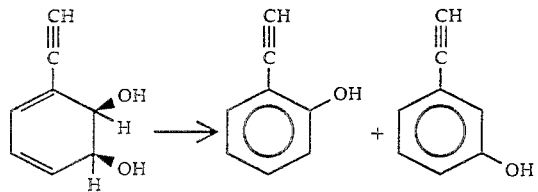

TABLE 1

| Treatment of Phenylacetylene Diol | Wt. % Products of Dehydration | |
|---|---|---|
| | 2-Hydroxy Phenylacetylene | 3-Hydroxy Phenylacetylene |
| 0.3N NaOH/RT/1 hr. | 58 | 42 |
| 0.6N NaOH/RT/1 hr. | 53 | 47 |
| 0.9N NaOH/RT/1 hr. | 51 | 49 |
| 0.9N NaOH/75° C./1 hr. | 11 | 89 |
| 1N HCl/RT/1 hr. | 95 | 5 |
| 1N NaOH/75° C./1 hr. | 4 | 96 |
| 1N HCl/RT/1 hr. | 93 | 7 |

EXAMPLE 2

Treatment of 2,3-dihydroxy-1-vinylcyclohexa-4,6-diene.

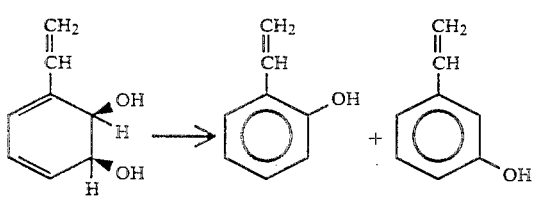

TABLE 2

| Treatment of Styrene Diol | Wt. % Products of Dehydration | |
|---|---|---|
| | 2-Hydroxy Styrene | 3-Hydroxy Styrene |
| 1N HCl/RT | 80 | 20 |
| 1N NaOH/RT | 77 | 23 |
| 1N NaOH/75° C. | 6 | 94 |
| 5N NaOH/75° C. | 0 | 100 |

EXAMPLE 3

Treatment of 2,3-dihydroxy-1-cycanocyclohexa-4,6-diene.

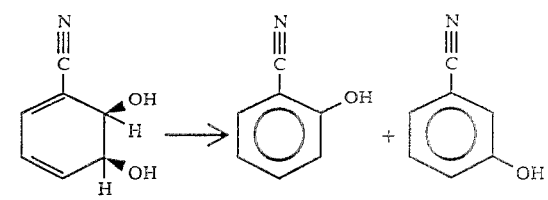

TABLE 3

| Treatment of Benzonitrile Diol | PPM Products of Dehydration | |
|---|---|---|
| | 2-Cyanophenol | 3-Cyanophenol |
| 1N HCl/RT/1 hr. | 14 | 11 |
| 1N HCl/75° C./1 hr. | 90 | 43 |
| 1N NaOH/RT/1 hr. | 0 | 158 |
| 1N NaOH/75° C./1 hr. | 0 | 0 |

EXAMPLE 4

Treatment of 2,3-dihydroxy-1-phenylcyclohexa-4,6-diene.

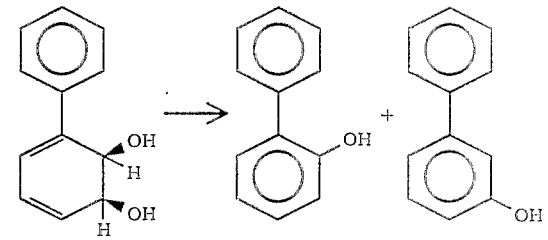

TABLE 4

| Treatment of Biphenyl Diol | PPM Products of Dehydration | |
|---|---|---|
| | 2-Phenyphenol | 3-Phenylphenol |
| 1N HCl/RT/1 hr. | 345 | 254 |
| 1N NaOH/RT/1 hr. | 293 | 121 |
| 1N NaOH/75° C./1 hr. | 49 | 402 |

We claim:

1. A process comprising treating an aqueous solution of a starting compound of the formula

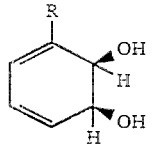

where —R is —CH=CH₂, —C≡CH [—C≡H], —C≡N or

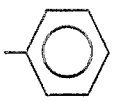

at a temperature of at least 20° C. with an aqueous basic solution at about the same temperature to bring the normality of the resulting basic solution to at least about 1.0 and maintaining the temperature about the same for at least 15 minutes and recovering a product principally of the formula

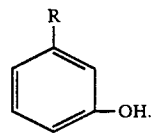

2. The process of claim 1 wherein the base is sodium hydroxide, potassium hydroxide or cesium hydroxide.

3. The process of claim 1 wherein —R is —C≡CH, —CH=CH₂ or

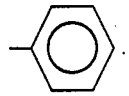

4. The process of claim 3 wherein the temperature is from about 75° to about 100° C.

5. The process of claim 4 wherein the basic solution is held at 75° to 100° C. for from about 1 to about 10 hours.

6. The process of claim 5 wherein from 200 to 5,000 ppm of the starting compound is present.

7. The process of claim 6 wherein —R is —C≡CH.

8. The process of claim 6 wherein —R is —CH=CH₂.

9. The process of claim 6 wherein —R is

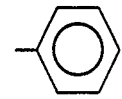

10. The process of claim 2 wherein —R is —C≡N and the temperature is 20° to 50° C.

* * * * *